United States Patent [19]
Breen

[11] Patent Number: 6,014,890
[45] Date of Patent: Jan. 18, 2000

[54] FAST RESPONSE HUMIDITY AND TEMPERATURE SENSOR DEVICE

[76] Inventor: Peter H. Breen, 6 Young Ct., Irvine, Calif. 92612

[21] Appl. No.: 08/935,366

[22] Filed: Sep. 22, 1997

Related U.S. Application Data

[60] Provisional application No. 60/027,484, Sep. 25, 1996.
[51] Int. Cl.$^7$ .............................. G01N 19/10; A61B 5/097
[52] U.S. Cl. .................. 73/29.02; 73/335.06; 73/335.08; 600/529; 600/543
[58] Field of Search ................................ 73/29.02, 29.05, 73/335.06, 335.03; 600/529, 532, 543

[56] References Cited

U.S. PATENT DOCUMENTS

| 2,189,855 | 2/1940 | Buffington et al. | 73/335.08 |
| 3,196,683 | 7/1965 | Gross | 73/335.08 |
| 3,603,135 | 9/1971 | Kawaguchi | 73/29.02 |

OTHER PUBLICATIONS

Farley et al., "Development of a probe for the in vivo measurement of airway humidity during anaesthesia," J.Biomed.Eng. 1990, vol. 12, Jul. 328–332.

Donaldson, "Methods for Measuring Sputum Viscosity and Inspired air Humidity in Tracheostomized Patients," Nursing Research, vol. 17, No. 5, pp. 388–395.

Tilling et al., "An accurate method of measuring medical humidifier output" Clin. Phys. Physiol Meas., 1983, vol. 4, No. 2, 197–209.

Shaw et al. "The Effect of and Correction for Different Wet–Bulb and Dry–Bulb Response in Thermocouple Physchrometry," J.of App'd Meteorology, vol. 19, Jan. 1980, 90–97.

Powell, "The Use of Thermocouples for Psychrometric Purposes," Proc. Phys.Soc., vol. 48, 406–414.

Ingelstedt, "Humidifying Capacity of the Nose," Ann. Otol-.Rhinol.Laryngol., vol. 79, 475–480.

Martin et al., "Comparing Two Heat and Moisture Exchangers with One Vaporizing Humidifier in Patients with Minute Ventilation Greater than 10 L/min," Chest vol. 107, May 5, 1995, 1411–1415.

Eisner et al., "Design and development of a micro–thermocouple sensor for determining temperature and relative humidity patterns within an airstream" Journal of Biomechanical Engineering, Nov. 1989, vol. 111 283–287.

Ingelstedt, "Studies on the Conditioning of Air in the Respiratory Tract," Acta Oto–Laryngologica Supplement, 1956, pp. 1–87.

Tsukamoto, "Dynamic Response of the Fine Wire Psychrometer for Direct Measurement of Water Vapor Flux," Journal of Atmospheric and Oceanic Technology, vol. 3, Sep. 1986, 453–461.

Kalogiros et al., "Fast–Response Humidity Measurements with the Psychrometric Method," Journal of Applied Meteorology, vol. 32, Sep. 1993, 1499–1507.

Davis, "Detailed Discussion of the Dry and Wet Bulf Psychrometer," Chapter III, ASHRAE Brochure on Psychrometry, ASHRAE Technical Committee on Psychrometrics (1969–1972) American Society of Heating Refrigerating and Air–Conditioning Engineers, Inc., 81–90.

(List continued on next page.)

*Primary Examiner*—Hezron Williams
*Assistant Examiner*—Daniel S. Larkin
*Attorney, Agent, or Firm*—Fulbright & Jaworski

[57] ABSTRACT

An airway humidity sensor incorporating a small, dry thermocouple and small, wet thermocouple to measure cyclical humidity in inspiration and expiration by the psychrometric principle, the psychrometric component incorporating dialysis micro-tubing in contact with the wet-bulb thermocouple junction, the thermocouples being offset from one another across the cross-sectional plane of the airway in a direction normal to the airflow.

18 Claims, 5 Drawing Sheets

OTHER PUBLICATIONS

Ingelstedt, "Aerodynamics Within the Larynx and Trachea," Acta oto–laryng.Suppl.158, 81–92.

Feihl et al., "The Temperature and Water Output of Heat and Moisture Exchangers During Synchronous Intermittent Mandatory Ventilation," Acta. Anaesth.Italica vol.43, Suppl. 1 57–64, 1992.

Chiranda, "Evaluation of a 3rd Generation Heat and Moisture Exchanger as an Alternative to Conventional Humidifiers in ICU," Acta. Anaesth.Italica vol. 43, Suppl. 1 73–76, 1992.

Jackson et al., "An Evaluation of the heat and moisture exchange performance of four ventilator circuit filters," Intensive Care Medicine (1992) vol. 18, 264–268.

Brackenbury et al., "Measurement of water loss in exercising animals using an electronic humidity detector," Med. & Biol. Eng. & Comp. 1982, vol. 20, 433–436.

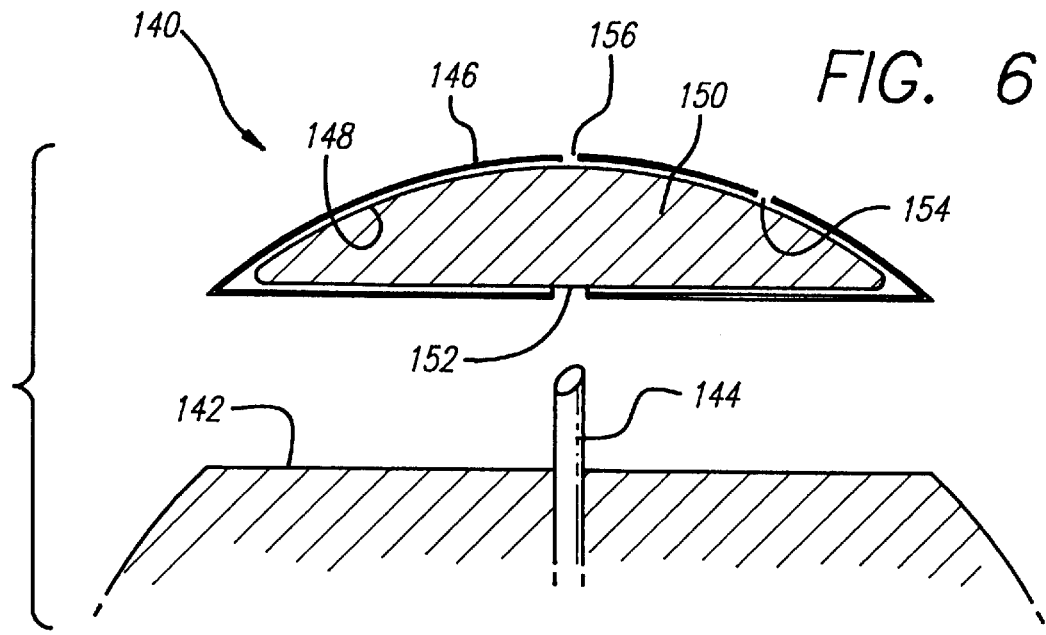
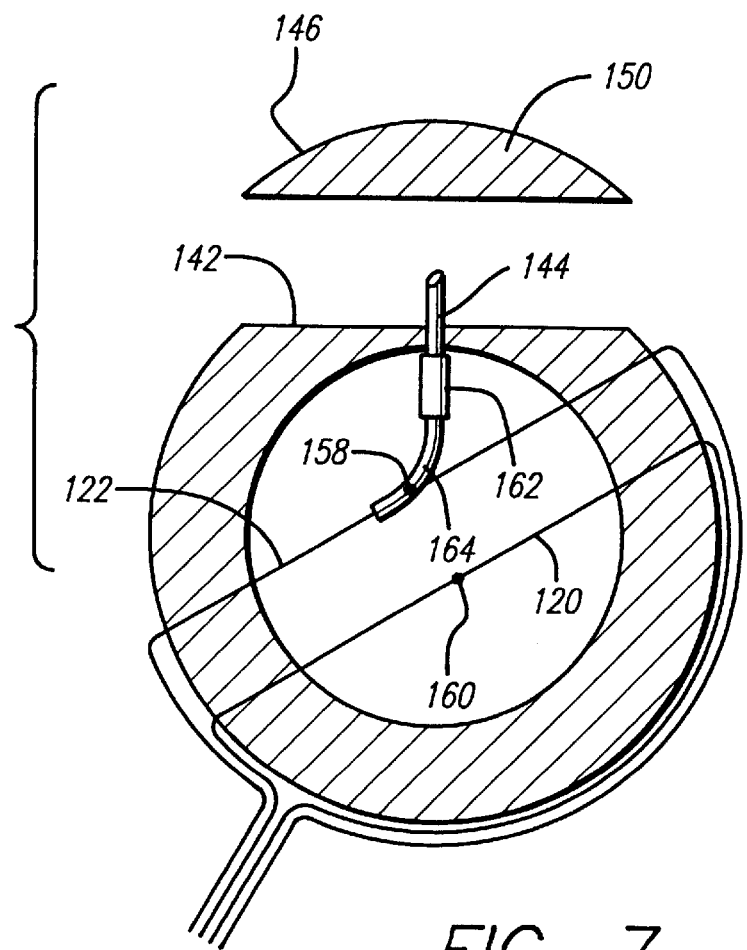

FAST RESPONSE HUMIDITY AND TEMPERATURE SENSOR DEVICE

This application claims the benefit of U.S. Provisional Application Ser. No. 60/027,484 filed Sep. 25, 1996.

This invention was made with Government support under Grant No. HL-42637, awarded by the National Institutes of Health. The Government has certain rights in this invention.

BACKGROUND AND SUMMARY OF THE INVENTION

The measurement of humidity in inspired and expired gas would be helpful in the management of patients undergoing anesthesia and critical care medicine. Oxygen consumption is commonly measured during steady state conditions by invoking the Haldane transformation (mass balance of nitrogen over the respiratory cycle) to calculate the increase in expired volume due to increased temperature and added water vapor. However, during high inspired $O_2$ breathing or during non-steady state conditions, mass balance for nitrogen cannot be used. Then, a direct measurement of humidity in inspired and expired gas, along with measurements of airway flow, $O_2$ fraction, and temperature could generate a measurement of $O_2$ consumption per breath ($V_{O2,br}$).

During mechanical ventilation of patients during anesthesia or critical care medicine, breath-by-breath measurements of gas humidity at the airway opening are rarely conducted. Current humidity sensors are bulky, respond slowly, and lack disposability due to their expense.

Other applications of a humidity sensor include:

1. Assessment of heat and water exchange during ventilation in anesthesia and critical care medicine, including the efficacy of humidifiers. Benefits of adequate inspired gas humidification include conservation of patient temperature, decreased airway mucosal drying (less inspissation of secretions and preservation of muco-ciliary transport and lung defense), and decreased cooling of airways (minimize provocation of bronchoconstriction).
2. Assessment of aerosol deposition and/or penetration of airborne pollutants. Many pollutants and medicinal aerosols are hygroscopic (i.e. have affinity for water vapor).
3. Airway thermometry measurement of cardiac output. The addition of airway humidity measurement may enhance the measurement of pulmonary blood flow by airway thermometry.
4. Industrial applications, such as monitoring ambient atmospheres in clean rooms (e.g. microelectronics), require inexpensive, fast response, accurate, and full water vapor range measurement of humidity.

There have been prior attempts to develop a probe for in vivo measurement of airway humidity during anaesthesia. See for example the two-wire capacitive absorption sensor described by Farley et al. in "Development of a probe for the in vivo measurement of airway humidity during anaesthesia," J.Biomed.Eng. 1990 Vol. 12, July, 328–332. The probe is located 20 cm into the airway, corresponding to the level of the mid-trachea. See also Donaldson, "Methods for Measuring Sputum Viscosity and Inspired Air Humidity in Tracheostomized Patients," Nursing Research, Vol. 17, No. 5, pp 388–395, wherein there is described a portable "pistol" and temperature indicating instrument in which a small fan draws air over two thermistors in a barrel, one of which is covered with a wet wick. A minimum of 30 seconds was required for each temperature reading.

The humidification of dry gas presented to the ventilated patient on an intensive therapy unit or during anaesthesia has been advocated by the medical profession for many years; see Tilling et al. "An accurate method of measuring medical humidifier output" Clin. Phys. Physiol Meas., 1983, Vol. 4, No. 2, 197–209, where the authors used a capacitance hygrometer.

The concept of differential wet-bulb and dry-bulb response in thermocouple physchrometry is well-established. Shaw et al. in "The Effect of and Correction for Different Wet-Bulb and Dry-Bulb Response in Thermocouple Physchrometry," J.of App'd Meteorology, Vol. 19, January 1980, 90–97 describes a wet-bulb sensor fabricated by wrapping one of the thermocouples with wicking compound obtained by separating the strands of cotton sewing thread. Water was supplied from a small reservoir while careful control of the flow rate was provided by "intravenous bag" flow rate adjustment on the tubing.

Powell in "The Use of Thermocouples for Psychrometric Purposes," Proc. Phys.Soc., Vol. 48, 406–414 describes the use of a thermocouple wrapped with very fine cotton for a distance of a centimeter on each side of the junction.

Ingelstedt in "Humidifying Capacity of the Nose," Ann. Otol.Rhinol.Laryngol. Vol. 79: 475–480 describes keeping a thermoelement moist using hygroscopic fibers.

Martin et al. in "Comparing Two Heat and Moisture Exchangers with One Vaporizing Humidifier in Patients with Minute Ventilation Greater than 10 L/min," Chest Vol. 107, May 5, 1995, 1411–1415, describes measuring humidity at the Y-piece of an inspiratory and expiratory line. They describe the use of two thermal probes, one wet and one dry, the upstream probe measuring the gas temperature, the downstream probe coated by sterile cotton wet with sterile water.

Eisner et al. in "Design and development of a micro-thermocouple sensor for determining temperature and relative humidity patterns within an airstream" Journal of Biomechanical Engineering, November 1989, Vol. 111 283–287, describes the use of a wetted miniature thermocouple coated with borom nitride to act as a wicking material.

Ingelstedt, in "Studies on the Conditioning of Air in the Respiratory Tract," Acta Oto-Laryngologica Supplement, 1956, pp 1–87 and attachments, describes a psychrometer in which the thermocouple wires are butt welded. The wet side wire was wrapped with rayon silk fibers, wound not only around the junction, but also along the wires at both sides of the junction to provide a hydroscopic material for the junction.

Other references discussing the problem of psychrometric measurement include:

Tsukamoto, "Dynamic Response of the Fine Wire Psychrometer for Direct Measurement of Water Vapor Flux," Journal of Atmospheric and Oceanic Technology, Vol. 3, September 1986, 453–461.

Kalogiros et al. "Fast-Response Humidity Measurements with the Psychrometric Method," Journal of Applied Meteorology, Vol.32, September 1993, 1499–1507.

Davis, "Detailed Discussion of the Dry and Wet Bulf Psychrometer," Chapter III, ASHRAE Brochure on Psychrometry, ASHRAE Technical Committee on Psychrometrics (1969–1972) American Society of Heating Refrigerating and Air-Conditioning Engineers, Inc., 81–90.

Ingelstedt, "Aerodynamics Within the Larynx and Trachea," Acta oto-laryng. Suppl.158, 81–92.

Feihl, "The Temperature and Water Output of Heat and Moisture Exchangers During Synchronous Intermittent Mandatory Ventilation," Acta. Anaesth.Italica Vol.43, Suppl. 157–64, 1992.

Chiranda, "Evaluation of a 3rd Generation Heat and Moisture Exchanger as an Alternative to Conventional Humidifiers in ICU," Acta. Anaesth.Italica Vol. 43, Suppl. 173–76, 1992.

Jackson, "An Evaluation of the heat and moisture exchange performance of four ventilator circuit filters," Intensive Care Medicine (1992) Vol. 18, 264–268.

Brackenbury, "Measurement of water loss in exercising animals using an electronic humidity detector," Med. & Biol. Eng. & Comp. 1982, Vol. 20, 433–436.

SUMMARY OF THE DISCLOSURE

An airway opening humidity sensor is provided that incorporates a small dry thermocouple and a small wet thermocouple to measure cyclical humidity in inspiration and expiration by the psychrometric principle, in which the amount of evaporative cooling is a function of the ambient relative humidity. In a particular embodiment, the humidity sensor is incorporated, either permanently or by adaptation into the Y-piece of an anaesthesia airway circuit. In one form of this embodiment, an adapter is provided to fit onto the base of the Y-piece which adapter includes the dry thermocouple and wet thermocouple and means for delivering water from a supply to the thermocouple junction of the wet thermocouple. In another form of the embodiment, the thermocouples and delivery means are built into the base of the Y-piece of the anaesthesia airway circuit.

In specific embodiments, the humidity sensor comprises a micro-psychrometer including dry and wet thermocouples, means for containing a supply of water, and tubing connected to the water supply means for delivering water to the junction of the wet thermocouple whereby to coat the thermocouple junction while enabling evaporation from the tubing. The tubing has a sufficiently small inner diameter to draw water from the supply by capillary action as water evaporates from the wet thermocouple junction. The tubing and thermocouple wire are arranged so that the thermocouple wire extends through the end of the tubing proximal its junction. Preferably the tubing is itself water permeable, most preferably being dialysis micro-tubing. In a further embodiment, the housing for the humidity sensor contains a separable reservoir of water. The reservoir comprises a compliant container and a semi-flexible support housing for the container. The conduit to the wet thermocouple junction is formed to include a component that is sufficiently rigid to pierce the container when it is in place.

BRIEF DESCRIPTION OF THE DRAWINGS

FIG. 6 is a cross-sectional view of the top portion of FIG. 5;

FIG. 7 is an exploded schematic cross-sectional view of the adapter of FIG. 5.

DETAILED DESCRIPTION OF THE INVENTION

Theory of Psychrometry.

Psychrometry is the principle whereby the measurement of gas humidity is determined from simultaneous dry bulb thermometer and wet bulb thermometer measurements. The dry bulb thermometer measures the temperature of the gas. The temperature of the wet bulb thermometer depends on both the temperature and humidity of the gas. The rate of evaporation of water from the wet bulb thermometer depends on the amount of water vapor present in the surrounding gas. The temperature of the wet bulb thermometer results from a balance between the evaporative cooling and convective heating by the ambient gas flows.

Wet-bulb and dry-bulb temperatures are digitally measured and relative humidity measurement proceeds by standard psychrometric equations. Water vapor pressure is calculated from the wet bulb and dry thermometers using the psychometric equation, $$e=e_s(T_w)-\gamma(T_d-T_w)$$

where c is the vapor pressure, $e_s(T_w)$ is the saturated vapor pressure at the wet bulb temperature $(T_w)$, and $\gamma=0.660$ mb/o C when barometric pressure is 1000 mb. Relative humidity is the ratio of actual water vapor present in gas to the maximum quantity which could saturate at the gas temperature. Thus, relative humidity (RH) is given by $$RH=100\times e/e_s(T_d)$$

Design of the Small Tube Micro Psychrometer.

Airway thermometers are constructed from thermocouples, which generate a voltage proportional to the temperature of the junction of two dissimilar metals. Thermocouples are chosen as the thermometer device for their small size, their stability, and their fast response to change in temperature.

Figure 1:
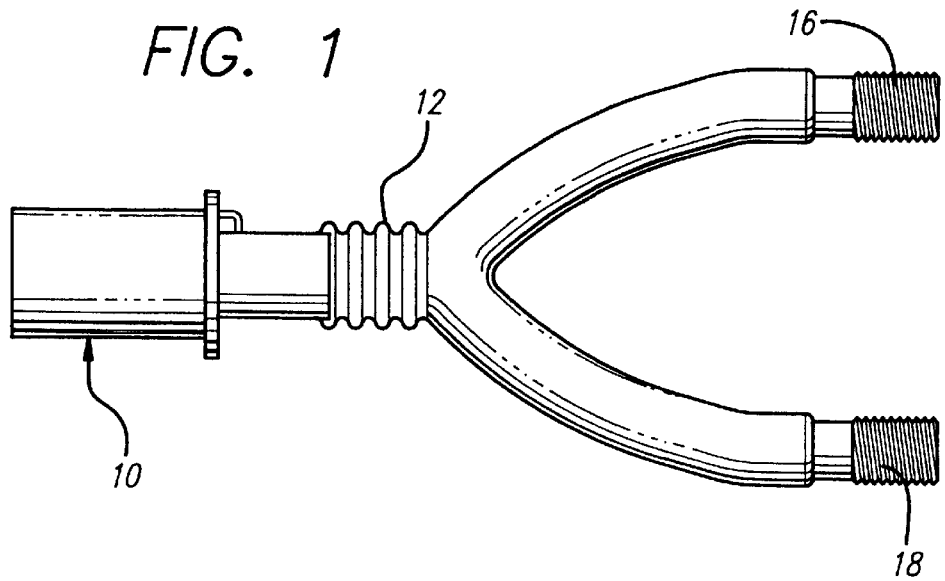
FIG. 1 is a schematic plan view of an adapter formed in accordance with this invention shown connected to the Y piece of an anaesthesia airway circuit.
Figure 2:
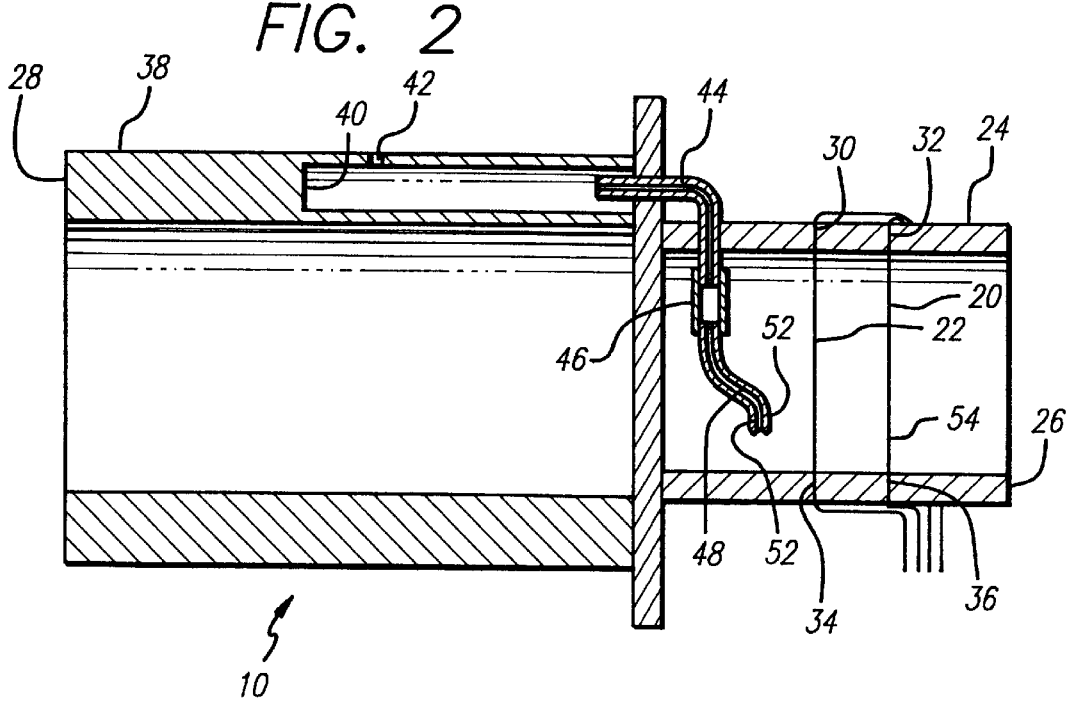
FIG. 2 is a cross-sectional schematic view of the adapter of FIG. 1.

Referring to FIG. 1, there is shown an adapter 10 constructed in accordance with this invention connected to the base 12 of the Y of a standard airway circuit. One leg 16 of the Y piece is for inspiration and the other leg 18 is for expiration. Referring to FIG. 2, the airway micropsychrometer consists of a dry thermocouple 20 (also referred to as a dry-bulb thermocouple) and a wet-bulb thermocouple 22 stretched across the cross-sectional diameter of the small end 24 of a standard airway adapter. The sizes of the ends 26 and 28 of the adapter 10 allow direct interposition in the breathing circuit at the airway opening. The dry and wet thermocouples 20 and 22 are longitudinally separated by 0.5 mm and are offset from each other across the cross-sectional diameter of the adapter in a direction normal to the airflow so that the dry thermocouple 20 is not affected by the wet-bulb thermocouple 22 as will be shown infra and discussed more clearly with regard to FIG. 7.

To construct the thermocouples, the bare ends of 40 gauge TEFLON insulated copper and constantan wire (Newport Electronics, Santa Ana, Calif., TFCP-003-5D, Type T, Special Limits of Error) are butt soldered, preferably, they are butt welded. Alternatively, they can be axially wound over each other (like strands of a rope) for a distance of 5 mm and soldered, albeit with an increase in thermal mass. The copper and constantan ends of the thermocouples exit through small holes 30, 32 and 34, 36 in opposite sides of the airway adapter 10, suspending the thermocouples across the diameter of the airstream. The short length of copper-constantan contact decreases the thermal mass of the thermocouples and minimizes effects of thermal radiation from the inside of the airway adapter case. The small size of the thermocouple wires (0.080 mm wire diameter) causes negligible obstruction of airflow but are sufficiently strong and rigid to withstand wind forces through the airway.

At their exit from the airway adapter, the copper and constantan wires of the thermocouples 20 and 22 are encased in a 1.4 mm plastic tube (not shown) for stress relief. For each thermocouple, the free end of the copper wire is connected to one-channel of a 2-channel DC amplifier. The free end of the constantan wire is soldered to a copper wire attached to the amplifier. This second copper-constantan junction is maintained in an ice bath at 0° C. to provide a cold reference thermocouple junction. If solder provides the connection between the wires of the thermocouple, the net thermocouple voltage of the copper-solder-constantan metal interfaces would still equal the copper-constantan thermocouple voltage.

The dual-channel analog amplifier circuit linearly boosts the thermocouples DC signal 5,000 fold. To maintain a high signal-to-noise ratio, an amplifier is used which incorporates op-amplifier technology (1458 Dual Op-Amp, Radio Shack, Fort Worth, TX) and a DC power source (pair of 9 V batteries). The use of a DC battery power supply facilitates portability, small amplifier footprint (about the size of a personal pager), no alternating current interference, and electrical safety for the patient (no risk of leakage of current from higher voltage and AC power sources). The amplified temperature signals are digitized by an analog-to-digital (A–D) conversion card (ADA2200, Real Time Devices, State College, Pa.) in a personal computer (80486 microprocessor, 66 MHz), driven by data acquisition software (Atlantis for DOS, Version 3.2, Lakeshore Technologies, Chicago, Ill.).

In a specific embodiment, to fit standard equipment, the small end of the airway adapter has an outer diameter of 15 mm and an inner diameter of 12 mm. The large end of the airway adapter has an outer diameter of 21 mm and an inner diameter of 15 mm. An endotracheal tube can connect to the larger end 38 of the adapter. Thus, inspired and expired gas both flow through the humidity sensor.

A reservoir 40 to contain water for application to the wet-bulb thermocouple, is formed in the wall of the large end 38 of the adapter 10. A small vent hole 42 allows injection of water, e.g., with a hypodermic needle, and venting during application to the thermocouple. A conduit tube 44 extends from the reservoir 40 and into the small end 24 of the adapter 10. The conduit 44 is connected through TYGON® microbore tubing 46 (300 $\mu$m ID) to hollow fiber dialysis tubing 48 (200 $\mu$m ID) 8 $\mu$m wall thickness; HEMOPHAN®, (Cobe Laboratories, Lakewood, Colo.). The wet-bulb thermocouple 22 is threaded through a hole 50 in the dialysis tubing proximal the thermocouple junction 52, which is spaced from the junction 54 of the dry-bulb thermocouple 20.

Water from the reservoir 40 flows through the conduit 44, through the micro-bore tubing 46, and through the hollow fiber dialysis micro-tubing 48. Where it wets the junction 52 of the wet-bulb thermocouple 22. Previous methods to maintain water over a wet-bulb thermocouple were difficult to manufacture, non-safe for patient use, or increased the thermal mass and consequently significantly degraded the response of the wet-bulb thermocouple. The present technique using water-permeable dialysis micro-tubing provides a new multi-feature method of water delivery to the wet-bulb thermocouple.

(a) The dialysis micro-tubing provides a very small water envelope over the wet-bulb thermocouple with resultant low thermal mass. Thus, the response time of the wet-bulb thermocouple is fast (time constant approximately equal to 0.2 seconds) and can measure cyclical inspired and expired humidity even during fast respiratory frequency.

(b) Because of its water permeable nature, the dialysis tubing provides both a conduit for water delivery to the wet-bulb thermocouple as well as a surface for evaporation.

(c) The small caliber of the dialysis tubing minimizes conductive heat transfer between the adapter housing and the wet-bulb thermocouple.

(d) As water evaporates, capillary action in the micro-tubing pulls water from the water reservoir and the wet-bulb thermocouple stays hydrated even during maximal drying conditions.

(e) All components can be made of non-toxic materials with demonstrated safety for patients.

During the low humidity gas flow of inspired air, the wet bulb thermocouple cools to a lower temperature than the dry thermocouple due to heat loss from evaporation. In the event of inadequate wet bulb hydration, the loss of full evaporative cooling results in an increase in wet bulb temperature that occurs abruptly over about five breaths. In contrast, excess application of water to the wet-bulb thermocouple causes a delayed response but preservation of the final wet-bulb temperature.

The response time of the humidity sensor to a step change in water vapor content is less than 0.5 second. The temperature response time is even quicker. Testing the device in a range of humidity and temperature standards demonstrates good agreement with published psychrometry tables. The measurement is stable and the surface envelope of the wet bulb thermocouple remained hydrated during long tests conducted over several hours.

Figure 3:
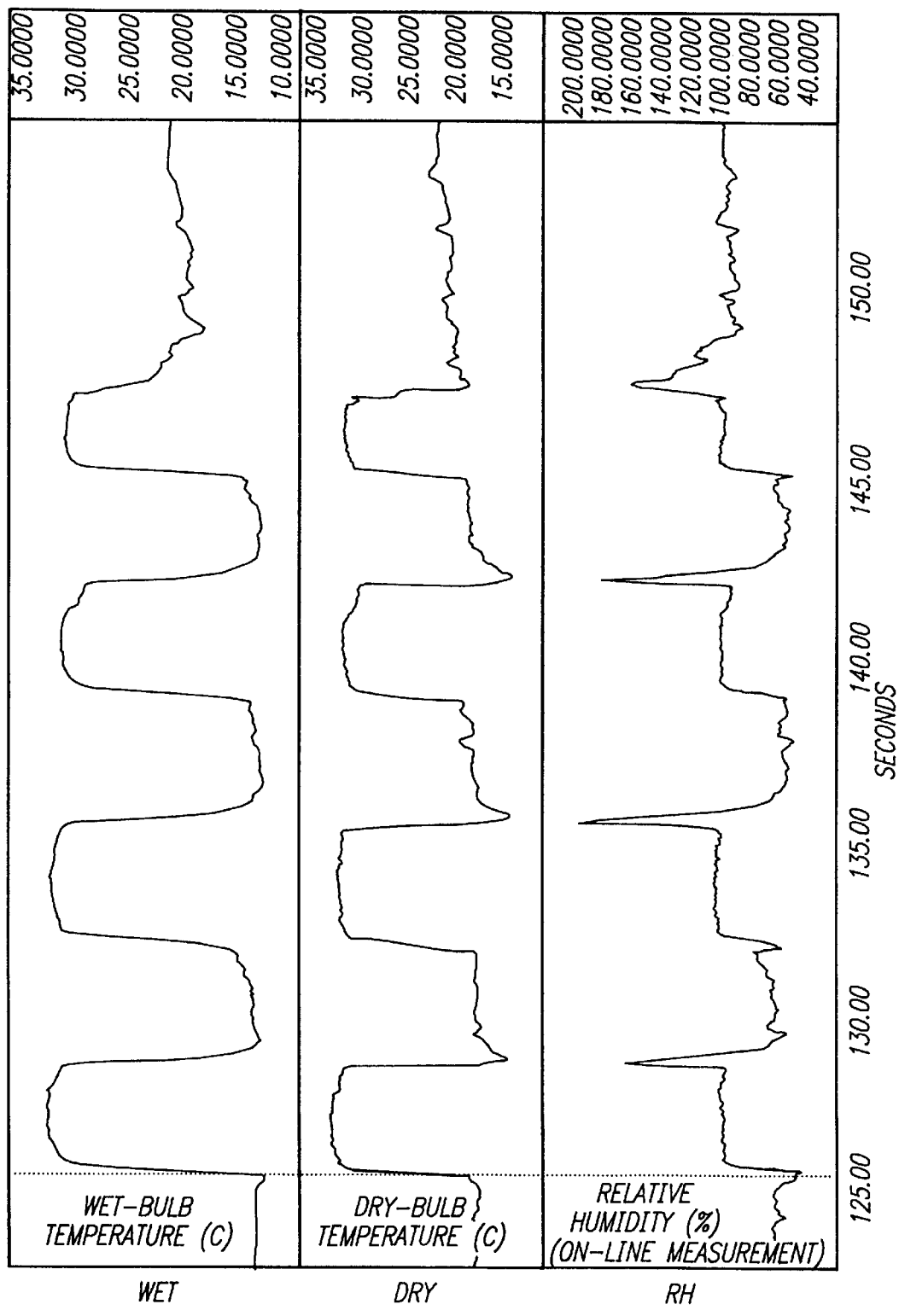
FIG. 3 is a graph showing wet-bulb temperature, dry-bulb temperature and relative humidity during cyclical breathing through the humidity sensor by a human subject.

FIG. 3 displays a plot of the wet-bulb temperature (° C. upper panel), dry-bulb temperature (middle panel), and relative humidity (%, lower panel) during cyclical breathing through the humidity sensor by a human subject. The wet bulb temperature displays a fast response to a change from expiration (Exp) to inspiration (Insp), where the time constant is about 0.2 second. The dry-bulb temperature has an even faster response, as a result of its smaller thermal mass.

Computer algorithms can determine on-line instant measurements of airway gas temperature, relative humidity, and absolute water vapor content. These measurements of airway gas temperature and water vapor content allow on-line and accurate determination of the measurement of standard temperature, pressure, and dry (STPD) volumes for both inspired air (cold and dry) and expired air (warm and humid) to correctly measure oxygen consumption in a patient model. For applications that require an even faster response for the wet-bulb thermocouple, a response enhancement can be provided. It can be shown, both theoretically and experimentally, that the response of the wet-bulb thermocouple to a step change in humidity conforms to a single-exponential function. Computer algorithms have been developed that enhance the response of the wet-bulb thermocouple by adding to the signal time at t, the product of the slope of the temperature-time function and the time constant. Such an algorithm uses the relation $T_c(t)=T_{(t)}+dT/$ dt·τ wherein $T_c$ is the corrected temperature at time t and τ is the time constant equal to the time that the signal takes to change 63% of its eventual total change.

Metabolic and gas exchange measurements in clinical medicine and physiological studies:

The measurement of oxygen consumption ($VO_2$) is an important monitor of normal cardiopulmonary and tissue function in anesthesia and critical care medicine. Because $\dot{V}O_2$ is the difference between inspired and expired volumes of $O_2$, normally the measurement of $\dot{V}O_2$ requires accurate assessment of inspired and expired volume. But, traditionally, it has been very difficult to measure the extra volume of expiration (compared to inspiration) because of the difficulty to measure the extra warmth and humidity of expired air. Often, an inert gas (usually nitrogen) is monitored since the ratio of inspired to expired nitrogen can allow the calculation of the ratios of inspired and expired volumes. However, this nitrogen technique (Haldane transformation) cannot be used if there is not enough nitrogen in the breathing circuit, such as during high oxygen fraction breathing in the intensive care unit or during anesthesia. The humidity and temperature sensor device of the present invention can continuously and immediately measure temperature and humidity of a gas sample and hence allow its correction to STPD conditions, with easy determination of $\dot{V}O_2$. The ability to measure $\dot{V}O_2$ on-line, along with the measurement of $\dot{V}CO_2$, can greatly enhance the monitoring of gas exchange during anesthesia, critical care medicine, pulmonary function and cardiovascular studies, and basic physiological investigations, to degrees that hitherto have not been possible. Other medical and physiological applications: There are other clinical and physiological arenas where the accurate and continuous measurement of airway gas humidity and temperature would be useful. For example, during anesthesia or critical care medicine, gaseous heat and water exchange measurements in the lung would be useful in body temperature control and lung mucosal hydration and barrier function, especially since a wide range of ventilation and humidification systems are in use. Another example is the study of aerosol deposition in the respiratory tract, which is dependent, among other things, on the airway gas humidity. Thus, the measurement and control of aerosol drug delivery systems can be optimized.

Varied industrial applications:

This inexpensive, accurate, responsive, and sensitive gas temperature and humidity sensor is useful in industrial applications anywhere climactic monitoring and control is important (e.g. electronic assembly plants), especially in situations where humidity is cyclically or quickly changing.

Figure 4:
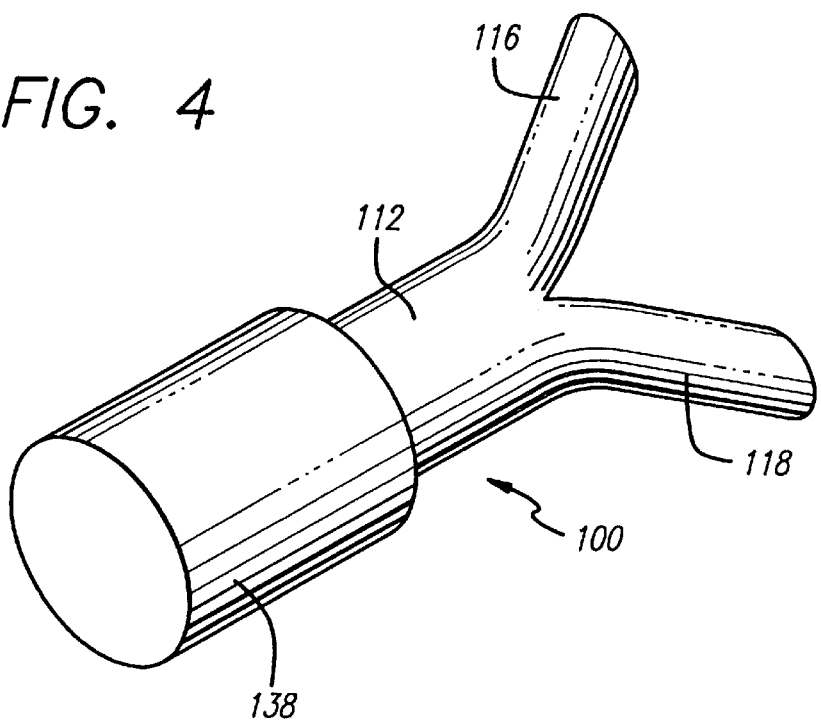
FIG. 4 is a schematic perspective view of another embodiment of this invention in which a humidity sensor of different construction is incorporated into the base of the Y-piece of an anaesthesia airway circuit.

Referring now to FIGS. 4 through 7, an embodiment is shown wherein there is provided a separable water reservoir. As shown in FIG. 4, a hollow airway Y piece 100 is molded so that its ends 116 and 118 form standard connectors to a standard anaesthesia airway circuit. The Y piece 100 connects to the inspiration and expiration lines 116 and 118 of the ventilating circuit. An endotracheal tube (not shown) connects to the larger, 15 mm inner diameter, end 138. Inspired and expired gases both flow through a humidity sensor as shown below, built into the Y piece at its base 112.

Figure 5:
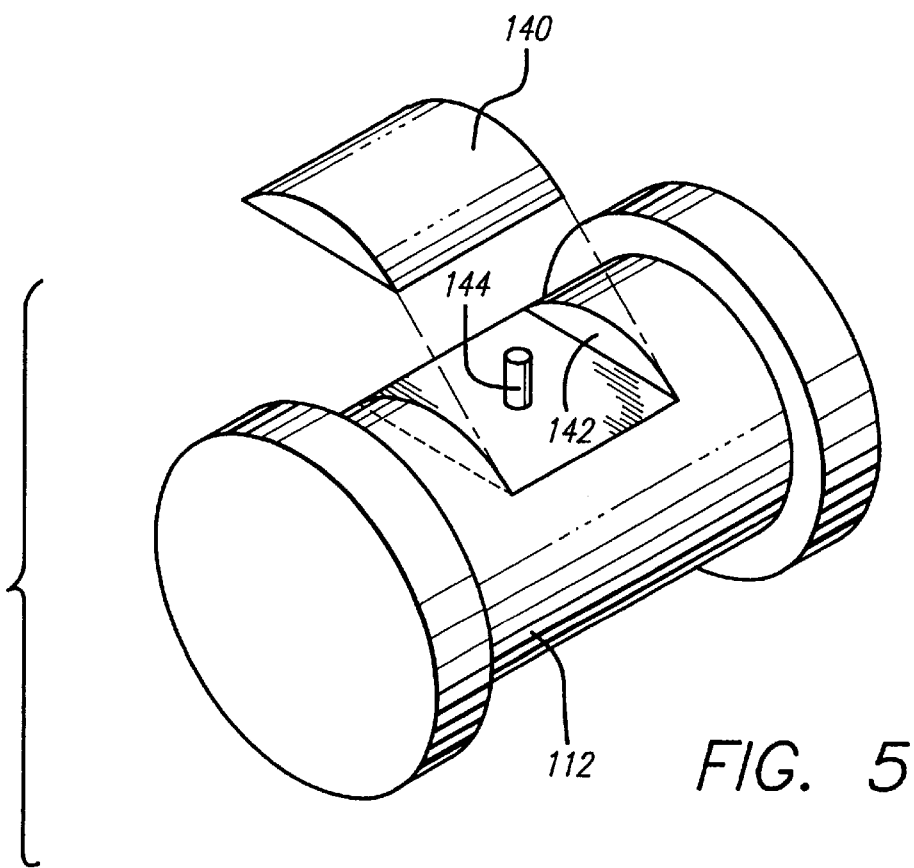
FIG. 5 is an exploded schematic perspective view of a portion of the base of FIG. 4.

The embodiment of FIGS. 4 through 7 incorporate a separable water reservoir 140 which snaps into a channel therefore 142 in the housing constituting the base 112. As shown in FIGS. 5 through 7 a hollow needle 144 punctures the water reservoir 140 to begin flow of water to the wet-bulb thermocouple 122. As shown in FIG. 6, the water reservoir consists of a housing 146 constructed of semiflexible plastic. A compliant plastic bag 148 which contains about 3 ml of water 150 forms an inner lining of the reservoir 140. The plastic bag 148 is attached to the reservoir housing 146 around a thin membrane 152 through which the hollow needle 144 pierces. The reservoir housing 146 is equipped with a one way flap-valve 154 and breathing or vent hole 156.

The wet-bulb thermocouple 122 with its junction 158 and dry-bulb thermocouple 120 with its junction 160 are as described with respect to FIG. 2 as are the TYGON® micro-bore tubing 162 and hollow fiber dialysis microtubing 164. As in FIG. 2, the wet-bulb thermocouple wire passes through the end of the dialysis microtubing 164 so that its junction 158 is within the dialysis micro-tubing, whereby the junction 158 is wetted by the water drawn by capillary force from the reservoir bag 148.

As evaporation from the wet-bulb thermocouple 122 draws water out of the reservoir bag 148, ambient air is entrained through the breathing hole 156 as the reservoir bag 148 collapses away from the reservoir housing 146. If necessary (e.g. during activation of the humidity sensor), water may be pumped through the hollow needle 144 and water delivery system to the wet-bulb thermocouple 122 by sealing the breathing hole 156 with a finger as the dome of the flexible reservoir housing 146 is depressed. Upon release of the reservoir housing dome, the one-way flap valve 154 insures that negative pressure (relative to barometric pressure) does not apply to the reservoir bag 148.

The modular water reservoir system as described herein has several features:

(a) The collapsible water reservoir plastic bag 148 permits a gas-free system in any position so that gas does not enter the water delivery system and cause an air lock in the micro-bore tubing.

(b) Entrainment of ambient air through the breathing hole of the reservoir housing allows the water reservoir 148 bag to collapse without imparting negative pressure (and decreased water flow) to the water delivery system.

(c) The breathing hole 156, one-way flap-valve 154, and flexible reservoir housing 146 provide a simple system to pump and flush water through the delivery system.

(d) The reservoir volume is 3 ml, which will provide adequate hydration to the wet-bulb thermocouple 122 for hours.

(e) If the water becomes depleted, the reservoir 140 can be replaced without interrupting ventilation. During this procedure, if a small amount of air is entrained into the water delivery system, then a water flush procedure can be conducted, as described above.

(f) The humidity sensor housing and water reservoir 140 can be packaged separately for ease of sterilization and long shelf life of the product. Activation of the humidity sensor is achieved as soon as the water reservoir is snapped into the channel 142 of the adapter housing.

Referring to FIG. 2 and FIG. 7, although these are different adaptations, the disposition of the thermocouple wires 20 and 22, on the one hand, and 120 and 122, on the other, are similar. In each case, the dry-bulb wet-bulb thermocouples are offset from each other in the middle of the cross-sectional plane of the airway in a direction normal to airflow direction. In this disposition, (FIGS. 2 and 7) the thermocouples can be positioned nearly beside each other, relative to the axial air flow while minimizing any downstream effects from one thermocouple on the other. Moreover, the orientation of the thermocouples strung across the adapter stabilizes their position in the airflow.

Early Version

Figure 8:
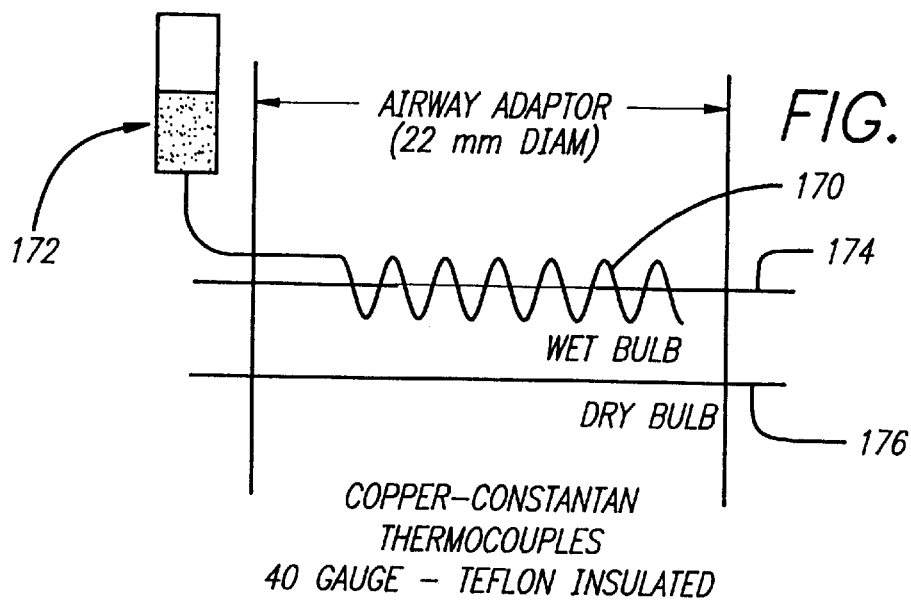
FIG. 8 is a schematic representation of a generalized form of the invention.

Referring to FIG. 8, there is shown a more generalized, abstract representation of an airway humidity sensor in accordance with some aspects of this invention. The sensor represents an early experimental stage in which cotton thread 170 (0.1 mm diameter) was spirally wrapped around the copper-constantan junction to provide a wicking mechanism to maintain a water envelope around the thermocouple. One end of the cotton thread was securely attached to the thermocouple; the other end of the cotton thread was threaded through a small plastic tube (I.D.≈0.5 mm), that entered the airway adapter lumen through a separate hole. The plastic tube was connected to a 1 mL syringe (Becton Dickinson & Co., Franklin Lakes, N.J.) containing distilled water.

In this embodiment an airway adapter of 22 mm of diameter was used with a syringe serving as a water reservoir 172 containing 1 ml of water to provide water drawn by capillary attraction to the cotton wick 170 wrapped around the wet-bulb thermocouple 174. Here too, the dry-bulb thermocouple 176 is offset from the wet-bulb thermocouple across the cross-sectional plane of the airway in a direction normal to the airflow.

By depressing the plunger of the syringe, the wet-bulb thermocouple was initially coated with a thin film of water. When water was present in the small plastic tube, the cotton thread absorbed enough water to keep the thermocouple hydrated for about one hour without manual plunger movement. The separate small tube water delivery system minimized thermal mass of the thermocouple, diminished convective heat transfer to the thermocouple, and helped equilibrate delivered water temperature (by exposure of the small tube inside the adapter to passing airflow) to the temperature of the wet-bulb thermocouple.

Figure 9:
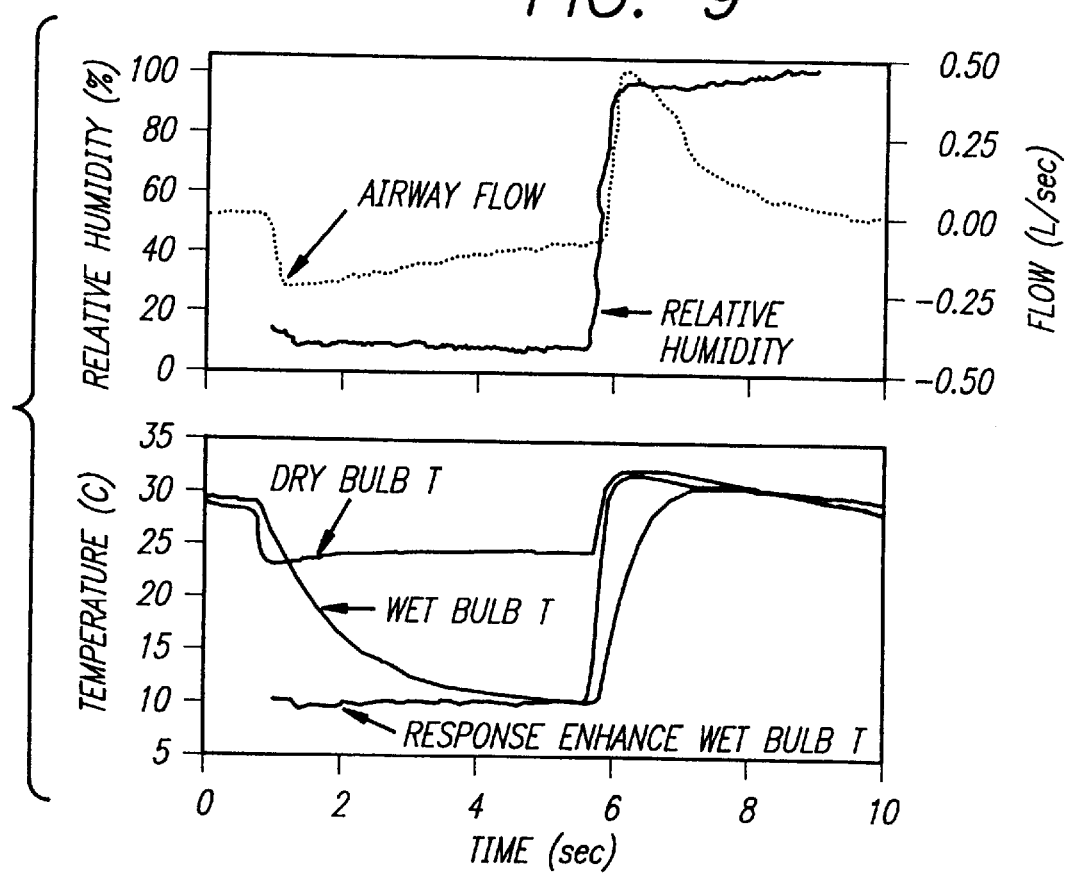
FIG. 9 is a plot of temperature, relative humidity and flow versus time in operation of the generalized embodiment.

The humidity sensor was validated against controlled humidity atmospheres over salt solutions (n=3), the results are set forth in Table I. The response of the dry thermocouple 20 is fast. In this early version, the wet-bulb thermocouple 174 τ was about 1 second and ≧0.25 L/s generated maximal time response. In a series of step increases and decreases in humidity and temperature in a bench setup demonstrated that the wet-bulb thermocouple 174 reacted with single exponential response. As shown in FIG. 9, a fit of the first 1 second of data (triangles in FIG. 9) allowed calculation of the final temperature (T), which closely agreed with the measured value.

TABLE I

|  | Saturated H20 | NaCl | Na Iodine | LiCl |
|---|---|---|---|---|
| RH: Expected (%) | 100 | 75 | 40 | 12 |
| RH: Measured (% ±SD) | 100.5 ± 4.9 | 77.8 ± 2.3 | 43.8 ± 2.3 | 13.5 ± 2.4 |

Legend:
RH = relative humidity; S.D. = standard deviation; NaCl = sodium chloride; Na Iodine = sodium iodine; LiCl = lithium chloride.

Validation of dynamic response (DR) correction of humidity/br in patients. After Institutional Review Board approval and informed written patient consent, the humidity sensor was interposed at the airway opening. During ventilator settings of an anesthetized patient that provided sufficiently long inspired time (FIG. 9), the wet-bulb T reached its minimum value (≈10° C.), identical to the predicted value from the early exponential T decay. Accordingly, the humidity sensor response should be suitable for fast respiratory frequency (with short inspiratory time), such as during pediatric ventilation. In this example, relative humidity (RH) was 9% during inspiration and 100% during expiration.

Effect of decreasing fresh gas flow (FGF) on inspired humidity in patients. In other patients during anesthesia, FGF into the circle circuit was decreased to 1.5 L/min. RH was as high as 50% at the beginning of inspiration due to addition of $H_2O$ vapor in the system from the patient's respiratory tract and from the $CO_2$ absorber (chemical reaction generates heat and water). As noted above, the difference in $H_2O$ vapor volume between the inspirate and expirate must be measured if the Haldane transformation can not be employed in the measurement of $V_{O2,br}$.

Effect of in-line humidifier. The commonly used in-line humidifier acts like an "artificial nose" by condensing and trapping moisture and heat on expiration and then re-delivering the water vapor by evaporation during the next inspiration.

During ventilation of anesthetized patients, we interposed an in-line humidifier at the airway opening on the ventilator side of the humidity sensor. During inspiration, RH never decreased below 75%.

Applying cotton fibers to the wet-bulb resulted in a low thermocouple volume to surface area ratio. The axial orientation with thin thermocouple wires (low heat conductivity) and suspension of the thermocouple across the airway adapter thermally isolates the thermocouple from latent heat of the adapter tube walls. Furthermore, this technique wicks water onto the thermocouple without increasing its thermal mass. Thus, the wet-bulb thermocouple has low thermal mass and size, large surface area-to-volume ratio, and large thermal isolation to allows the device to be responsive at low gas flows. Even so, gas flow through the adapter can be throttled down to a lower cross-sectional area with variable inlet orifice collars. Then, the same gas flow rate will have increased gas velocity over the wet-bulb thermocouple with presumed even faster response time of the device. Accordingly, the wet-bulb thermocouple, unlike other present slower devices, has a response time adequate even for cyclical gas flows that occur during clinical ventilation at higher respiratory frequencies.

The embodiments of this invention provide various advantages. The pressurized water capillary tube delivery system is thermally isolated from the wet-bulb thermocouple and keeps it wet indefinitely even in maximum gas drying conditions. In addition, the device facilitates confirmation of adequate wet-bulb hydration by confirming a temperature plateau.

A numerical determination of humidity per breath is obtained as follows:

Apply zero and gain adjustment to the electrical potentials of dry bulb and wet bulb temperatures.

Response enhance the digital wet bulb temperature signal by processing the first 1 second of data through an exponential function with extrapolation to the final (but not measured) wet bulb temperature.

Process digital signals of dry bulb temperature and response-enhanced wet bulb temperature through psychrometric equations and/or look-up table to generate humidity measurement.

If simultaneous gas flow measurements are available, convert inspired and expired volumes (time integral of flow)to STPD (standard temperature and pressure, dry) with correction (as necessary) for response time of the measuring system.

In General

Unlike other humidity measurement technologies which lose accuracy at higher humidities, this device can measure accurately the whole range of humidity. The tiny size of the device allows measurement right in the gas stream and does not itself affect the humidity which it is trying to measure. In particular, any gas sampling to measure humidity often introduces large errors from direct effects on humidity of the sampling apparatus (e.g. rain-out of water vapor on cool tubes). Thermocouple technology is very stable and calibration would not even be necessary if the adapter with wet-bulb and dry-bulb thermocouples was exchanged. The small size of the humidity and temperature sensor allows the device to function as a "sling psychrometer" when placed in standard gas flow humidity conditions.

Measurement of humidity by micro-psychrometry is stable, requires no zero reference or gain calibration, and measures the entire range of humidity. Only a reliable, fast measurement of temperature is required, which is ably provided by thermocouples.

Thermocouples output a voltage potential proportional to temperature that is unique and stable for a given pair of contacting metals. Over the temperature range required for psychrometry, the voltage versus temperature function is linear so that a two-point temperature calibration of the thermocouple that spans the range of temperature is the only calibration required for the thermocouples. Within the constraint of precision of thermocouple manufacturing, this means that a given copper-constantan thermocouple can be exchanged for another without repeating the calibration.

By means of the instant invention, a humidity sensor can be constructed which is sufficiently inexpensive to facilitate single use followed by disposal. The device is designed for maximum patient safety. No toxic materials are used. In particular, previous attempts at wet-bulb thermocouples have used boron nitride as a wicking material, which although inert, can still break off and lodge in the lung. The thermocouples are suspended from both sides for safety. Then, if one wire breaks (signaled by loss of temperature signal), the thermocouple will not be inhaled into the lung. The cost of all raw materials for the temperature and humidity sensor (excluding the computer) is low. Prototype construction has occurred in a standard laboratory with basic electrical and mechanical engineering techniques that easily extrapolate into mass manufacturing of the device.

Accordingly, this new, inexpensive, small, stable, responsive low dead space humidity and temperature sensor can be easily incorporated into many medical, physiological, and industrial applications, to measure rapid changes in humidity that hitherto have not been possible. For example, the addition of the sensor to the airway circuit will allow most anesthesia ventilators for the first time to accurately measure complex metabolic values.

What is claimed is:

1. An airway humidity sensor for measuring the humidity of a gas flow, comprising:
   a psychrometer including first and second spaced thermocouples, each formed by the junction of dissimilar metal wires for measuring, respectively, the wet-bulb and dry-bulb temperatures of said gas flow;
   means for containing a supply of water;
   tubing having one end connected to said water supply means and the other end adjacent the junction of said first thermocouple for delivering water to the junction of said first thermocouple whereby to coat said first thermocouple junction while enabling evaporation therefrom, said tubing having a sufficiently small inner diameter to draw water from said supply by capillary action as water evaporates from said first thermocouple junction.

2. The airway humidity sensor of claim 1 in which said thermocouples are offset from one another across the cross-sectional plane of the airway in a direction normal to airflow.

3. The airway humidity sensor of claim 1 in which said first thermocouple extends through the end of said tubing proximal the junction of said thermocouple.

4. The airway humidity sensor of claim 1 in which said tubing is water permeable, whereby to provide an evaporative surface.

5. The airway humidity sensor of claim 4 in which said tubing is dialysis micro-tubing.

6. The airway humidity sensor of claim 1 disposed in a housing having a reservoir for said water supply and including a conduit for connecting to said reservoir and to said tubing whereby to deliver water from said reservoir to said tubing.

7. The airway humidity sensor of claim 6 in which said reservoir is separable from said housing.

8. The airway humidity sensor of claim 7 in which said reservoir comprises a container of water, said conduit being sufficiently rigid to pierce said container when said container is placed on said housing.

9. The airway humidity sensor of claim 8 in which said water container is compliant and said reservoir comprises a support housing therefor, said container support housing having a bottom wall connecting to said psychrometer housing, a top wall, and an opening in said bottom wall for said conduit.

10. The airway humidity sensor of claim 9 in which said support housing has a one-way flap in said top wall and a vent opening in said top wall, to allow air respectively to enter and escape said support housing.

11. The airway humidity sensor of claim 6 in which said housing is of a size to connect to the base of the Y-piece of anaesthesia airway circuit.

12. The airway humidity sensor of claim 6 in which said housing constitutes at least a portion of the base of the Y-piece of an anaesthesia airway circuit.

13. An adapter for the base of the Y-piece of an anaesthesia airway circuit, containing a psychrometer comprising first and second thermocouples in said adapter, each thermocouple formed by the junction of dissimilar metal wires for measuring, respectively, the wet-bulb and dry-bulb temperatures of gas flow through said Y-piece, said thermocouples being offset from one another across the cross-sectional plane of the airway in a direction normal to the airflow, said adapter including:
   means for containing a supply of water; and
   means for delivering water from said supply to the junction of said first thermocouple whereby to coat said first thermocouple junction while enabling evaporation therefrom.

14. A base for the Y-piece of an anaesthesia airway circuit, containing a psychrometer comprising first and second spaced thermocouples, in said base, each formed by the junction of the similar materials, for measuring respectively, the wet-bulb and dry-bulb temperatures of gas flow through said Y-piece, said thermocouples being offset from one another across the cross-sectional plane of the airway in a direction normal to the airflow, said base including:
   means for containing a supply of water; and
   means for delivering water from said supply to the junction of said first thermocouple whereby to coat said first thermocouple junction while enabling evaporation therefrom.

15. An airway humidity sensor for measuring the humidity of a gas flow, comprising:

a psychrometer including first and second spaced thermocouples, each formed by the junction of dissimilar metal wires for measuring, respectively, the wet-bulb and dry-bulb temperatures of said gas flow;

means for containing a supply of water;

water permeable dialysis micro-tubing connected to said water supply means for delivering water to the junction of said first thermocouple whereby to coat said first thermocouple junction while enabling evaporation therefrom, said tubing having a sufficiently small inner diameter to draw water from said supply by capillary action as water evaporates from said first thermocouple junction.

16. An airway humidity sensor for measuring the humidity of a gas flow, comprising:

a housing;

a psychrometer in said housing including first and second spaced thermocouples, each formed by the junction of dissimilar metal wires for measuring, respectively, the wet-bulb and dry-bulb temperatures of said gas flow;

a container of water for placement in said housing;

a conduit for connecting to said container of water, said conduit being sufficiently rigid to pierce said container when said container is placed on said housing;

tubing connected via said conduit to said container of water for delivering water to the junction of said first thermocouple whereby to coat said first thermocouple junction while enabling evaporation therefrom, said tubing having a sufficiently small inner diameter to draw water from said supply by capillary action as water evaporates from said first thermocouple junction.

17. An airway humidity sensor for measuring the humidity of a gas flow, comprising:

a housing of a size to connect to the base of the Y-piece of an anesthesia airway circuit and having a reservoir for a supply of water;

a psychrometer in said housing including first and second spaced thermocouples, each formed by the junction of dissimilar metal wires for measuring, respectively, the wet-bulb and dry-bulb temperatures of said gas flow;

tubing connected to said water supply means for delivering water to the junction of said first thermocouple whereby to coat said first thermocouple junction while enabling evaporation therefrom, said tubing having a sufficiently small inner diameter to draw water from said supply by capillary action as water evaporates from said first thermocouple junction.

18. An airway humidity sensor for measuring the humidity of a gas flow, comprising:

a housing constituting at least a portion of the base of the Y-piece of an anesthesia airway circuit and having a reservoir for a supply of water;

a psychrometer in said housing including first and second spaced thermocouples, each formed by the junction of dissimilar metal wires for measuring, respectively, the wet-bulb and dry-bulb temperatures of said gas flow;

tubing connected to said water supply means for delivering water to the junction of said first thermocouple whereby to coat said first thermocouple junction while enabling evaporation therefrom, said tubing having a sufficiently small inner diameter to draw water from said supply by capillary action as water evaporates from said first thermocouple junction.

* * * * *

UNITED STATES PATENT AND TRADEMARK OFFICE
CERTIFICATE OF CORRECTION

PATENT NO. : 6,014,890
DATED : January 18, 2000
INVENTOR(S) : Peter H. Breen

It is certified that error appears in the above-identified patent and that said Letters Patent is hereby corrected as shown below:

| COLUMN | LINE | |
|---|---|---|
| 1 | 57 | Change "in vivo" --*i n vivo* -- |
| 4 | 27 | Change "where c" to -- where e -- |
| 4 | 28 | Change "o" to -- o -- |

Signed and Sealed this

Thirteenth Day of February, 2001

Attest:

NICHOLAS P. GODICI

*Attesting Officer*  *Acting Director of the United States Patent and Trademark Office*